(12) United States Patent
Yu et al.

(10) Patent No.: US 6,861,048 B2
(45) Date of Patent: Mar. 1, 2005

(54) DENTIFRICE COMPOSITIONS HAVING REDUCED ABRASIVITY

(75) Inventors: Dahshen Yu, Randolph, NJ (US); Rita M. Parikh, Paramus, NJ (US); Charles Pozzi, Denville, NJ (US); Bruce Kohut, Toms River, NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 319 days.

(21) Appl. No.: 10/208,732

(22) Filed: Jul. 29, 2002

(65) Prior Publication Data

US 2003/0026768 A1 Feb. 6, 2003

Related U.S. Application Data

(63) Continuation of application No. 09/704,427, filed on Nov. 2, 2000, now abandoned, which is a continuation-in-part of application No. 09/288,828, filed on Apr. 8, 1999, now Pat. No. 6,221,340.

(51) Int. Cl.[7] ............................................... A61K 7/16
(52) U.S. Cl. ....................................................... 424/49
(58) Field of Search ..................... 424/49–88

(56) References Cited

U.S. PATENT DOCUMENTS

| | | | |
|---|---|---|---|
| 3,989,814 A | * 11/1976 | Cordon, I et al. ............. | 424/57 |
| 4,100,269 A | 7/1978 | Pader et al. | |
| 4,144,322 A | * 3/1979 | Cordon, IV et al. ........... | 424/49 |
| 4,170,634 A | * 10/1979 | Cordon, II et al. ............ | 424/49 |
| 4,187,288 A | * 2/1980 | Cordon, III et al. ........... | 424/49 |
| 4,309,409 A | * 1/1982 | Coll-Palagos et al. ......... | 424/52 |
| 4,416,867 A | * 11/1983 | Ritchey, I et al. ............. | 424/49 |
| 4,425,325 A | * 1/1984 | Ritchey, II et al. ............ | 424/54 |
| 4,545,979 A | 10/1985 | Ambike et al. | |
| 4,550,018 A | 10/1985 | Ambike et al. | |
| 4,562,063 A | * 12/1985 | Hayes, I et al. ............... | 424/49 |
| 4,562,065 A | * 12/1985 | Hayes, II et al. .............. | 424/49 |
| 4,562,066 A | * 12/1985 | Hayes, III et al. ............. | 424/52 |
| 4,568,540 A | * 2/1986 | Asano et al. ................... | 424/52 |
| 4,774,078 A | * 9/1988 | Curtis et al. ................... | 424/52 |
| 4,863,722 A | * 9/1989 | Rosenthal ...................... | 424/49 |
| 4,988,498 A | * 1/1991 | Evans et al. ................... | 424/52 |
| 5,059,416 A | 10/1991 | Cherukuri et al. | |
| 5,094,843 A | 3/1992 | Mazzanobile et al. | |
| 5,298,238 A | 3/1994 | Hussein et al. | |
| 5,330,748 A | * 7/1994 | Winston et al. ................ | 424/49 |
| 5,723,106 A | 3/1998 | Buch et al. | |
| 5,811,079 A | * 9/1998 | Yu, I et al. .................... | 424/52 |
| 5,817,295 A | 10/1998 | Chaudhari et al. | |
| 5,891,422 A | 4/1999 | Pan et al. | |
| 5,942,211 A | * 8/1999 | Harper et al. .................. | 424/49 |
| 5,948,390 A | 9/1999 | Nelson et al. | |
| 6,221,340 B1 | * 4/2001 | Yu, II et al. ................... | 424/49 |

FOREIGN PATENT DOCUMENTS

| | | |
|---|---|---|
| CA | 834131 | 2/1970 |
| EP | 0316079 | 5/1989 |
| GB | 2100983 | 1/1983 |
| WO | WO9603109 | 2/1996 |
| WO | WO9740812 | 11/1997 |
| WO | WO9811867 | 3/1998 |

* cited by examiner

*Primary Examiner*—Shep K. Rose
(74) *Attorney, Agent, or Firm*—Evan J. Federman; Darryl C. Little

(57) ABSTRACT

A method for reducing an abrasivity of a dentifrice composition containing an abrasive, includes incorporating into the dentifrice composition a zinc salt in an amount sufficient to reduce a dentinal abrasivity of the composition by at least 10% and reduce an enamel abrasivity of the dentifrice composition by at least 10%. The method provides an improved dentifrice composition, which is at least 90% as effective at stain removal as the original dentifrice composition. Suitable zinc salts include, e.g., zinc citrate, zinc chloride, zinc acetate, zinc oxide and zinc sulfate. Suitable abrasives include, e.g., silica, alumina and alkali metal meta-phosphates.

14 Claims, No Drawings

US 6,861,048 B2

DENTIFRICE COMPOSITIONS HAVING REDUCED ABRASIVITY

CROSS-REFERENCE TO RELATED APPLICATIONS

This is a continuation of Ser. No. 09/704,427 filed Nov. 2, 2000 now abandoned, which is a continuation-in-part of U.S. patent application Ser. No. 09/288,828 filed on Apr. 8, 1999 and now U.S. Pat. No. 6,221,340.

BACKGROUND OF THE INVENTION

1. Field of the Invention

The present invention relates to dentifrice compositions having reduced abrasivity. Specifically, the invention is directed to a method for reducing the abrasivity of dentifrice compositions employing an abrasive system and at least one zinc salt.

2. Description of Related Art

It has been difficult heretofore to provide dentifrices for use in the daily brushing and cleaning of teeth which provide a desirable balance of cleaning and polishing actions. This has been largely due to the difficulty in selecting suitable abrasives which afford maximum removal of difficult stains and debris without damaging the oral hard tissues.

The function of an abrasive substance in formulations intended for use in the oral cavity is to remove various deposits, including pellicle film, from the surface of the teeth. Pellicle film is a tightly adherent film which often contains brown or yellow pigments and imparts an unsightly appearance to the teeth. An advantageous abrasive material for incorporation into dental formulations should maximize film removal without causing undue abrasion to the hard tooth tissues. The typical soft abrasives used in dental compositions, such as dicalcium phosphate and calcium phosphate, although not unduly abrasive to tooth tissue, are not as effective as the hard abrasives in removing these undesirable deposits from the teeth. However, hard abrasives can cause serious problems when present in dental preparations since their outstanding abrasive characteristics are likely to cause undue abrasion to the oral hard tissues (enamel, dentin and cementum).

Others have attempted to address the problem of decreasing the abrasivity of dentifrices. For example, U.S. Pat. No. 4,102,992 discloses dentifrice compositions comprising water-insoluble organic polymers, such as thermoplastic acrylics (polymethyl methacrylate and polyisobutyl methacrylate), cellulosics, polyamides, polyethylene, polystryrene and the vinyls, which are less abrasive than calcium carbonate polishing agent.

U.S. Pat. No. 4,828,833 discloses dentifrice compositions in which a water soluble, linear polymer having a molecular weight above 1,000,000 effects a substantial reduction in dentin abrasivity and improves stain removal.

U.S. Pat. No. 4,144,322 discloses the reduction of enamel abrasiveness in dentifrices comprising a dental abrasive system of hydrated siliceous abrasive and the hard abrasive calcined alumina, and about 1–5% by weight of a calcium, magnesium or sodium salt, which effects a reduction in the radioactive (or relative) enamel abrasion (REA) of the dentifrice.

U.S. Pat. No. 4,407,788 and British Patent No. 2,100,983B disclose a siliceous polishing material and a small amount of a water soluble resinous poly(ethylene oxide) and maltitol humectant, which improve stain removal without raising radioactive (or relative) dentin abrasion (RDA).

Despite the foregoing developments, there is still room in the art for improved dentifrice compositions. In particular, it is desired to provide a method for reducing the abrasivity of dentifrice compositions without unduly hindering their cleaning efficacy. It is also desired to provide dentifrice compositions prepared according to such a method.

SUMMARY OF THE INVENTION

A method for reducing an abrasivity of a dentifrice composition containing an abrasive, includes incorporating into the dentifrice composition a zinc salt in an amount sufficient to reduce a dentinal abrasivity of the composition by at least 10% and reduce an enamel abrasivity of the dentifrice composition by at least 10%. The method provides an improved dentifrice composition, which is at least 90% as effective at stain removal as the original dentifrice composition.

DETAILED DESCRIPTION OF PREFERRED EMBODIMENTS

While the prior art discloses low pH toothpastes and other dentifrice compositions that contain zinc, the inventors are not aware of any prior art teaching that increasing zinc concentration decreases abrasivity without unduly hindering cleaning efficacy. The method and dentifrice of the invention benefit from this surprising and unexpected results associated with increased zinc concentration.

In embodiments, dentinal abrasivity is reduced by at least 10%, preferably at least 20%, more preferably at least 30% (as measured, for example, by the Relative Dentinal Abrasivity procedure described in the Examples, below).

In embodiments, enamel abrasivity is reduced by at least 10%, preferably at least 50%, more preferably up to about 80% (as measured, for example, by the Relative Enamel Abrasivity procedure described in the Examples, below).

The invention is especially surprising in that the decreased abrasivity is not necessarily accompanied by a reduction in stain removal efficacy. Thus, the invention is able to provide an improved dentifrice composition, which is at least as effective at stain removal as an unimproved version of the same dentifrice composition.

Dentifrices according to the invention preferably comprise a zinc salt selected from the group consisting of zinc citrate, zinc chloride, zinc acetate, zinc oxide and zinc sulfate. The zinc salt is preferably added in an amount from about 0.01 to about 3.0 wt. % (the expression "wt. %" as used herein denotes percentage by weight of the total weight of composition unless otherwise indicated), more preferably from about 0.02 to about 0.7 wt. %, even more preferably, from about 0.05 to about 0.5 wt. %, most preferably from about 0.1 to about 0.3 wt. %.

The pH for preferred embodiments of the present invention is from about 3.0 to about 5.5. A pH greater than about 5.5 has been found to decrease the antiseptic activity of the dentifrice composition.

The pH of the claimed dentifrice is adjusted to below 5.5 using suitable food or pharmaceutical grade acidifiers. These could include, but are not limited to, at least one of the following acidifiers: phosphoric acid, benzoic acid, citric acid, or other tricarboxylic acids, and the like. The most preferred acidifiers in the present invention include a mixture of phosphoric acid (from about 0.01% w/w to about 3.0% w/w, preferably in the range of from about 0.1% w/w to about 1.5% w/w, and most preferably in the range of from about 0.2% w/w to about 0.75% w/w); monobasic sodium phosphate (from about 0.01% w/w to about 1% w/w, preferably from about 0.1% w/w to about 0.5% w/w, and most preferably from about 0.2% w/w to about 0.4% w/w); dibasic sodium phosphate (from about 0.001% w/w to about 1.0% w/w, preferably from about 0.01% w/w to about 0.5% w/w, and most preferably from about 0.01% w/w to about 0.05% w/w); and benzoic acid (from about 0.01% w/w to about 1.0% w/w, preferably from about 0.05% w/w to about 0.5% w/w, and most preferably from about 0.08% w/w to about 0.35% w/w). The exact amount of acidifier added will depend on the final pH and buffer capacity desired.

The pH of the products may be buffered with salts of the acids in question. Common buffer systems include phosphoric acid and sodium phosphate salts, or citric acid and sodium citrate. Suitable buffers for use in this invention include citric acid-sodium citrate, phosphoric acid-sodium phosphate, sodium monobasic phosphate, sodium dibasic phosphate, acetic acid-sodium acetate, succinic acid-sodium succinate, aconitic acid-sodium aconitate and benzoic acid-sodium benzoate in amounts up to about 1% w/w, preferably from about 0.05% w/w to about 0.75% w/w of the composition, and most preferably from about 0.1% w/w to about 0.5% w/w of the composition.

Dentifrice compositions of this invention also contain, but are not limited to, one or more of the following dentifrice additives: abrasives, surfactants, binders and thickeners, humectants, sweeteners, desensitizing agents, flavors, colors, and preservatives. The preceding active ingredients and additives are combined in a hydrous or anhydrous vehicle to form a solid (i.e. toothpowder), a semi-solid (i.e. paste or gel), or a liquid.

Preferred dentifrice compositions according to the present invention contain anti-microbial agents and one or more fluoride-releasing compounds that provide anticaries activity. One class of anti-microbial agent known for use in dentifrice is the non-cationic anti-microbial agent. A substantially water-insoluble anti-microbial agent has a solubility in water at 25° C. of less than 1%, preferably less than 0.5% and more preferably less than 0.1%. The anti-microbial agents employed in certain dentifrice compositions of this invention can be regarded as essentially non-ionic in character. However, many suitable anti-microbial compounds contain one or more phenolic hydroxy groups that may be ionizable at certain pHs. A more exact description of the general class of anti-microbial agents useful in certain dentifrice compositions of this invention is that they are non-cationic in nature.

Examples of classes of non-cationic anti-microbial agents that may be employed in the dentifrice composition of the invention are phenolic and bisphenolic compounds, halogenated diphenyl ethers, benzoate esters and carbanilides.

Illustrative of the phenolic anti-microbial compounds, which include the halogenated salicylanilides, are 2-phenylphenol, 4-chlorophenol, 4-chloro-2-methylphenol, 4-chloro-3-methylphenol, 4-chloro-3,5-dimethylphenol, 2,4-dichloro-3,5-dimethylphenol, 3,4,5,6-tetrabromo-2-methylphenol, 5-methyl-2-pentylphenol, 4-isopropyl-3-methylphenol, 5-chloro-2-hydroxydiphenylmethane, 4',5-dibromosalicylanilide, 3,4',5-trichlorosalicylanilide, 3,4',5-tribromosalicylanilide, 2,3,3',5-tetrachlorosalicylanilide, 3,3',4,5'-tetrachlorosalicylanilide, 3,5-dibromo-3'-trifluoromethylsalicylanilide and 5-n-octanoyl-3'-trifluoromethylsalicylanilide.
Suitable bisphenolic compounds include 2,2'-methylenebis (3,4,6-trichlorophenol), 2,2'-methylenebis (4-chlorophenyl) 2,2'-methylenebis(4-chloro-6-bromophenol), bis(2-hydroxy-3,5-dichlorophenyl) sulphide and bis(2-hydroxy-5-chlorophenyl) sulphide.

In embodiments, these antibacterial agents can be employed in the form of their zinc derivatives, many of which are disclosed in U.S. Pat. No. 4,022,880.

Exemplifying the class of the halogenated hydroxydiphenyl ethers are the compounds 2',4,4'-trichloro-2-hydroxydiphenyl ether and 2,2'-dihydroxy-5,5'-dibromo-diphenyl ether.

Another well-known class of non-cationic anti-microbial agents are the esters of p-hydroxybenzoic acid, especially the methyl, ethyl, propyl, isopropyl, butyl, isobutyl, hexyl, heptyl and benzyl esters.

Halogenated carbanilides can also be used in embodiments, which class is typified by 3,4,4'-trichlorocarbanilide, 3-trifluoromethyl-4,4'-dichlorocarbanilide and 3,3',4-trichlorocarbanilide.

Other known substantially water-insoluble non-cationic anti-microbial agents can also be used, for example 2,4-dichlorobenzyl alcohol, 3,4-dichlorobenzyl alcohol and 3-(4-chlorophenoxy)-propan-1,2-diol.

The above-mentioned anti-microbial agents that are suitable for use in dentifrices are not antibiotics. Antibiotics are preferably avoided so as to avoid the risk of resistant strains of bacteria developing. The anti-microbial agent will usually be used in an amount of 0.01 to 5%, preferably 0.05 to 1% by weight of the dentifrice. A mixture of anti-microbial agents may, of course, be used.

Preferred dentifrice compositions according to the present invention can also include essential oils. Essential oils are volatile aromatic oils that are synthetic or are derived from plants by distillation, expression or extraction. Essential oils usually carry the odor or flavor of the plant from which they are obtained. If used in the dentifrice compositions of this invention, essential oils provide anti-gingivitis activity. Some of these essential oils also act as flavoring agents. The essential oils of this invention include, but are not limited to, thymol, menthol, methyl salicylate (wintergreen oil) and eucalyptol.

Thymol, also known by the chemical formula 5-methyl 2-(1-methylethyl) phenol, is obtained from the essential oil of *Thymus vulgaris Labiatae* and *Monarda punctata Labiatae*. Thymol is a white crystalline powder with an aromatic odor and taste. Thymol is soluble in organic solvents but only slightly soluble in deionized water.

Menthol is isolated principally from the oil of *Mentha arvensis*. In its commercial form, menthol is available as L-menthol crystals obtained from a process involving cooling of the oil. Fractional distillation of peppermint oil that usually contains from about 40% to about 65% menthol represents another important source of menthol. Synthetic sources of L-menthol are also available.

Eucalyptol is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels.

Methyl salicylate is the main ingredient in many essential oils, constituting about 99% of oil of wintergreen (*Gaultheria procumbens*) and sweet birch (*Betula lenta*). Methyl salicylate, which has a distinctive refreshing aroma, is used widely in mouthwashes, chewing gums and other oral and pharmaceutical preparations.

The amounts of essential oils that can be used in the dentifrice compositions of the present invention are from about 0.46% to about 0.5623% thymol, about 0.4644% to about 0.5676% methyl salicylate, about 0.306% to about 0.374% menthol and about 0.6971% to about 0.8519% eucalyptol, wherein said amounts are clinically effective in inhibiting gingivitis. More preferably a dentifrice according to the present invention contains about 0.5112% thymol, about 0.5160% methyl salicylate, about 0.34% menthol and about 0.7745% eucalyptol, wherein said amounts are clinically effective in inhibiting gingivitis.

Fluoride-releasing compounds are preferably used in the dentifrice compositions of the present invention. These compounds may be fully or slightly water soluble, release fluoride ions or fluoride-containing ions in water and do not react with other components in the composition. It is well known that dentifrice compositions containing fluoride-releasing compounds help prevent dental caries. Typical fluoride-releasing compounds are inorganic fluoride salts such as water-soluble alkaline earth metal, alkali metal, and heavy metal salts. Sodium monofluorophosphate, sodium fluoride, stannous fluoride and mixtures of these compositions are preferred.

The amount of fluoride-releasing compound present in the dentifrice compositions of this invention must be nontoxic. The specific amount depends upon the type of fluoride-releasing compound employed, the solubility of the fluoride-releasing compound and the formulation of the dentifrice composition. In general, the fluoride-releasing compound will be present in an amount by weight of up to about 1.2% w/w, preferably from about 0.1% w/w to about 1.0% w/w, and most preferably from about 0.175% w/w to about 0.8% w/w of the dentifrice composition so as to provide 800–1500 ppm fluoride ion.

Surfactants or surface active agents are organic compounds that reduce surface tension between liquids and aid in the dispersion of a composition throughout the oral cavity. The surfactant in the present invention may be anionic, nonionic, or amphoteric. The oral hygiene or dentifrice compositions of the present invention may contain surfactants in amounts up to about 5.0% w/w; preferably from about 0.1% w/w to about 3.0% w/w of the dentifrice composition; and most preferably from about 0.2% w/w to about 2.0% w/w of the dentifrice composition.

The most preferred surfactants are anionic. These anionic surfactants include, but are not limited to, sodium lauryl sulfate, sodium lauroyl sarcosinate, sodium methyl cocoyl taurate, and disodium lauryl sulfosuccinate. A preferred surfactant is sodium lauryl sulfate. The compositions according to the present invention are substantially free from one or more highly pure alkali metal salts of dodecyl sulphate having less than 5% non-dodecyl alkyl sulphate salts.

Amphoteric surfactants have the capacity to behave as either an acid or a base and include quaternized imidazole derivatives. Preferred amphoteric surfactants include long chain (alkyl) amino-alkylene aklylated amine derivatives, also known as MIRANOL®, manufactured by Rhone-Poulanc, Cranberry, N.J.

Natural and artificial sweeteners may be used in the dentifrice compositions. The sweetener may be selected from a wide range of well known materials including naturally occurring water-soluble sweeteners, artificial water-soluble sweeteners and modified water-soluble sweeteners derived from naturally occurring water-soluble sweeteners. Artificial water-soluble sweeteners include, but are not limited to, soluble saccharin salts, e.g., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin and dipeptide based sweeteners, such as L-aspartic acid derived sweeteners. Dipeptide sweeteners include L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenylalanine and L-aspartyl-L-(1-cyclohexene)-alanine. Naturally occurring water-soluble sweeteners include, but are not limited to, sugar alcohols, including sorbitol as 70% sorbitol solution, mannitol, xylitol, maltitol, hydrogenated starch hydrolysates and mixtures thereof.

Water-soluble sweeteners derived from naturally occurring water-soluble sweeteners include, but are not limited to, chlorinated derivatives of sucrose, known, for example, under the product designation of Sucralose; and protein-based sweeteners such as thaumaoccous danielli (Thaumatin I and II).

Sorbitol solution supplies sweetness and body to the composition and gives a desirable mouth feel. Sorbitol solution also enhances flavor, prevents harsh taste and provides a fresh and lively sensation in the mouth. It also prevents caking of the dentifrice.

In general, an effective amount of sweetener is utilized to provide the level of sweetness desired in any particular embodiment of the dentifrice compositions according to the present invention. This amount will vary with the sweetener selected and the final form of the composition. The amount of sweetener normally present is from about 0.0025% w/w to about 60% w/w of the dentifrice composition. The exact range of amounts for each type of sweetener in a dentifrice is readily determined by those skill in the art.

The flavors that may be used in the invention include natural and artificial flavors known in the dentifrice art. Suitable flavors include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils that are used widely as flavoring agent and antiseptic and was found useful in masking the harsh taste of thymol.

The amount of flavor is normally a matter of preference subject to the type of final dentifrice composition, the individual flavor employed and the strength of flavor desired. The flavors are preferably utilized in amounts that may range from about 0.01% w/w to about 6% w/w of the dentifrice composition. The flavors used in the compositions according to the present invention comprise flavoring oils that are not substantially free of terpenes.

Coloring agents are used in amounts effective to produce a dentifrice of the desired color. These coloring agents may be incorporated in amounts up to about 3% by weight of the dentifrice composition. The coloring agents may also include natural food colors and dyes suitable for food, drug and cosmetic applications. These coloring agents are known as FD & C dyes and lakes. The coloring materials are preferably water-soluble. Illustrative nonlimiting examples include the indigoid dye known as FD & C Blue No.1, and D & C Yellow No. 10. A full recitation of all FD & C colorants and their corresponding chemical structures may be found in the Kirk-Othmer Encyclopedia of Chemical Technology, 3rd Edition, in volume 5 at pages 857–884. A preferred opacifier, titanium dioxide, may be incorporated in amounts up to about 2.0% w/w, preferably less than about 1.0% w/w of the composition and most preferably less than about 0.4% w/w.

Suitable humectants in this invention include sorbitol, as 70% sorbitol solution, glycerin, propylene glycol, polyethylene glycol, mixtures thereof, and the like. Humectants may be present in amounts from about 1.0% to about 75.0% by weight of the dentifrice composition.

Suitable abrasive substances for use in this invention must be compatible with the low pH of the composition and include hydrated silica, alumina or alkali metal metaphosphates. Silica abrasives in the dentifrice composition according to this invention may include among others, ZEODENT® (113), manufactured by J. M. Huber Corp. and SYLOID® or SYLODENT®, manufactured by W. R. Grace Co. These polishing agents may be used in amounts up to about 75.0% w/w of the composition, preferably in amounts from about 5.0% w/w to about 40% w/w of the composition and most preferably from about 5.0% w/w to about 30.0% w/w of the composition.

The dentifrice composition includes an oral vehicle that can be a paste, gel, powder or liquid. Depending upon the specific form of the dentifrice, the composition may also include thickeners, binders or gelling agents to provide a desired consistency. Gelling agents such as hydroxyethyl cellulose, carboxymethyl cellulose, methyl cellulose, xanthan gum, gelling silicas and the like may be used singly or in combination. The preferred gelling system is a mixture of carboxy methyl cellulose, xanthan gum and gelling silica. Gelling agents may be used in amounts from about 0.5% w/w to about 30% w/w, preferably from about 5.0% w/w to about 15.0% w/w of the dentifrice composition, and most preferably from about 7.0% w/w to about 20% w/w of the composition.

The dentifrice composition of this invention may also contain a desensitizing agent such as strontium chloride, potassium nitrate or sodium citrate-citric acid, which may be used in an amount from about 0.5% w/w to about 10% w/w.

Suitable preservatives include benzoic acid, butylated hydroxyanisole (BHA), butylated hydroxytoluene (BHT), ascorbic acid, methyl paraben, propyl paraben, tocopherols and mixtures thereof. Preservatives when used are generally present in amounts up to about 1.0% w/w, and preferably from about 0.1% w/w to about 1.0% w/w of the dental gel composition.

The present invention is further illustrated by the following non-limiting examples. All parts and percentages in the examples and throughout the specification and claims are by weight of the final composition unless otherwise specified.

EXAMPLES 1–2 AND COMPARATIVE EXAMPLE

Dentifrice compositions were formulated with the ingredients listed in Table 1 using the following protocol:

(a) add 60% of sorbitol and 90% of water to tank (Hobart Mixer);

(b) dissolve in (a) sodium monofluorophosphate, sodium saccharin, sodium phosphate monobasic, sodium phosphate dibasic, polyethylene glycol, zinc citrate, FD&C Blue #1, D& C Yellow #10 and benzoic acid, with mixing until dissolved (about ten minutes);

(c) mix phosphoric acid with remaining water and add to (b) with mixing;

(d) blend Zeosyl 200, Sylodent 750 and titanium dioxide and add to (c), mixing for fifteen minutes;

(e) add remaining sorbitol to (d);

(f) blend carboxymethylcellulose and xanthan in glycerin and add to (e), mixing for forty minutes;

(g) add flavors to (f), mixing for five minutes;

(h) add sodium lauryl sulfate to (g), mixing slowly for ten minutes; and (i) deacrate under 25 to 27 in Hg for ten minutes.

TABLE 1

| INGREDIENT | EXAMPLE 1* | EXAMPLE 2* | COMPARATIVE EXAMPLE* |
| --- | --- | --- | --- |
| pH | 4.5 | 4.5 | 4.5 |
| Thymol | 0.5112 | 0.5112 | 0.5112 |
| Methyl Salicylate | 0.516 | 0.516 | 0.516 |
| Menthol | 0.34 | 0.34 | 0.34 |
| Eucalyptol | 0.7745 | 0.7745 | 0.7745 |
| Glycerin | 6 | 6 | 6 |
| Sorbitol (70%) | 40 | 40 | 40 |
| Water | 23.491 | 22.491 | 24.491 |
| Peg 1450 | 3 | 3 | 3 |
| Xanthan Gum | 0.25 | 0.25 | 0.25 |
| Na Carboxymethyl Cellulose | 1.2 | 1.2 | 1.2 |
| Flavor | 0.225 | 0.225 | 0.225 |
| Sodium MFP | 0.76 | 0.76 | 0.76 |
| Na Saccharin | 1.2 | 1.2 | 1.2 |
| $NaH_2PO_4$ | 0.25 | 0.25 | 0.25 |
| $Na_2HPO_4$ | 0.03 | 0.03 | 0.03 |
| Zinc Citrate | 1 | 2 | 0 |
| $TiO_2$ | 0.35 | 0.35 | 0.35 |
| Gelling Silica | 11 | 11 | 11 |
| Abrasive Silica | 7 | 7 | 7 |
| Sodium Lauryl Sulfate | 1.5 | 1.5 | 1.5 |
| Phosphoric Acid | 0.45 | 0.45 | 0.45 |
| Benzoic Acid | 0.15 | 0.15 | 0.15 |
| Color | 0.0022 | 0.0022 | 0.0022 |

*Values are in wt. %

The pastes prepared in accordance with Table 1, as well as several gels prepared in a similar fashion, were tested for abrasivity using the following conventional tests.

Relative Dentinal Abrasivity

Virtually all dentifrice products contain abrasive systems to aid in the removal and prevention of dental stains. Abrasivity testing of dentifrice formulations is recommended to document the safety of the products. A relative dentinal abrasivity (RDA) score of under 250 is regarded as acceptable by the American Dental Association. RDA values of commercially available dentifrices range from approximately 45 to 170, with some specialty products ranging as high as 230. This study used the Hefferren method (Hefferren, "A laboratory method for assessment of dentifrice abrasivity," J Dent Res 55:563–573 (1976)) to assess the RDA values of the test and reference products.

Samples of human dentine were cut and irradiated in a neutron flux to render them radioactive. The specimens were mounted in methylmethacrylate and placed in tubes of dentifrice slurry mounted in a V-8 mechanical cross brushing machine.

Sample tubes were filled with 1:1.6 dentifrice:water slurries, and the specimens were brushed for 1500 strokes under 150 g of brush pressure.

After brushing, aliquots of the slurry were taken for determination of radioactivity release. Higher levels of radioactivity reflect higher levels of dentinal attrition. All test products were normalized to the values obtained with a slurry of ADA reference abrasive, which was set to 100. The results are shown in Table 2.

TABLE 2

RDA RESULTS

| | 0% Zn | 1% Zn | 2% Zn |
|---|---|---|---|
| Gel | 137 | 98.36 | 74 |
| Paste | 141 | 105.8 | 77 |

Relative Enamel Abrasivity

A relative enamel abrasivity (REA) score of less than 20 is regarded as acceptable by the ISO (the International Organization for Standardization). This study used the Hefferren method (Hefferren, 1976) to assess the REA values of the test and reference products.

Samples of human enamel were cut and irradiated in a neutron flux to render them radioactive. The specimens were mounted in methylmethacrylate and placed in tubes of dentifrice slurry mounted in a V-8 mechanical cross brushing machine. Sample tubes were filled with 1:1.6 dentifrice-:water slurries, and the specimens were brushed for 5000 strokes under 150 g of brush pressure. After brushing, aliquots of the slurry were taken for determination of radioactivity release. Higher levels of radioactivity reflect higher levels of enamel attrition. All test products were normalized to the values obtained with a slurry of ADA reference abrasive, which was set to 10. The results are shown in Table 3.

TABLE 3

REA RESULTS

| | 0% Zn | 1% Zn | 2% Zn |
|---|---|---|---|
| Gel | 6.6 | 1.8 | 1.7 |
| Paste | 5.7 | 1.8 | 1.7 |

Stained Pellicle Reduction (SPR)

The ability of a dentifrice to remove an extrinsic stain is one of its more important attributes. This study employed a laboratory test measuring removal of preformed extrinsic stain from bovine teeth in vitro. Previous studies (J. Dent Res 61: 1236, 1982) have indicated that the results of this test compare quite favorably with those obtained in controlled clinical trials. Thus, the results of this test may be considered to predict clinical findings with a reasonable degree of confidence.

Samples of bovine enamel were cut and mounted in methylmethacrylate, subjected to a stain accumulation procedure, then scored for pretreatment stain intensity. The samples were then placed in tubes of dentifrice slurry mounted in a V-8 mechanical cross brushing machine. Sample tubes were filled with 1:1.6 dentifrice:water slurries, and the specimens were brushed for 800 strokes under 150 g of brush pressure. After brushing, the enamel samples were scored for stain. The stain reduction relative to pretreatment values was calculated. The results are shown in Table 4.

TABLE 4

SPR RESULTS

| | 0% Zn | 1% Zn | 2% Zn |
|---|---|---|---|
| Gel | 84 | 82 | 86 |
| Paste | 80 | — | 82 |

It can be seen from the results that compositions according to the invention have reduced abrasivity (Tables 2–3) with uncompromised stain removing ability (Table 4).

While the invention has been described in detail and with reference to specific examples thereof, it will be apparent to one skilled in the art that various changes and modifications can be made therein without departing from the spirit and scope thereof.

What is claimed is:

1. A method for reducing an abrasivity of a dentifrice composition comprising:
   a.) an abrasive selected from the group consisting of silica, alumina, alkali metal meta-phosphates
   b.) an antimicrobial agent; and
   c.) a phosphoric acid—sodium phosphate, sodium monophosphate, or sodium dibasic phosphate buffer, said method comprising incorporating into said dentifrice composition zinc citrate in an amount sufficient to reduce a dentinal abrasivity of said composition by at least 20% to provide an improved dentifrice composition, wherein said improved dentifrice composition is at least 90% as effective at stain removal as said dentifrice composition wherein the pH of the composition is below about 5.5% and wherein the antimicribial agent is non-cationic.

2. The method according to claim 1, wherein a pH is from 3.0 to 5.5.

3. The method according to claim 1, wherein said abrasive is present at a concentration of at least 5 wt. % of said dentifrice composition.

4. The method according to claim 1, wherein said amount of said zinc citrate is from 0.01 wt. % to 3.0 wt. % of said dentifrice composition.

5. The method according to claim 1, wherein said amount of said zinc salt is from 0.02 wt. % to 0.7 wt. % of said dentifrice composition.

6. The method according to claim 1, wherein said amount of said zinc salt is from 0.05 wt. % to 0.5 wt. % of said dentifrice composition.

7. The method according to claim 1, wherein said amount of said zinc salt is from 0.1 wt. % to 0.3 wt. % of said dentifrice composition.

8. The method according to claim 1, wherein said dentinal abrasivity is reduced by at least 30%.

9. The method according to claim 1, wherein said dentinal abrasivity is reduced by at least 30%.

10. The method according to claim 9, wherein said improved dentifrice composition is at least as effective at stain removal as said dentifrice composition.

11. The method according to claim 10, wherein said dentifrice composition further comprises:
    0.01 to 5.0 wt. % of an anti-microbial agent;
    0.1 to 1.2 wt. % of at least one fluoride-releasing compound;
    0.1 to 5.0 wt. % of at least one surfactant;
    0.5 to 30.0 wt. % of at least one thickener;
    1.0 to 75.0 wt. % of at least one humectant;
    0.0025 to 60 wt. % of at least one sweetener;
    0.5 to 10.0 wt. % of at least one desensitizing agent;
    0.01 to 6.0 wt. % of at least one flavoring agent;
    0 to 3.0 wt. % of at least one coloring agent;
    0 to 2.0 wt. % of at least one opacifier;
    0 to 1.0 wt. % of at least one preservative; and
    a buffering system including an acid and at least one corresponding salt.

12. The method of claim 11, wherein:
    said anti-microbial agent is a member selected from the group consisting of phenolic compounds, bisphenolic compounds, halogenated diphenyl ethers, benzoate esters and carbanilides;

said fluoride-releasing compound is a member selected from the group consisting of water-soluble alkaline earth metals, alkali metals and heavy metal salts;

said surfactant is a member selected from the group consisting of sodium lauryl sulfate, sodium lauroyl sarcosinate, sodium methyl cocoyl taurate, disodium lauryl sulfosuccinate, quaternized imidazoles and (alkyl) amino-alkylene alkylated amines;

said thickener is at least one member selected from the group consisting of hydroxyethyl cellulose, carboxymethyl cellulose, methyl cellulose, xanthan gum and gelling silica;

said humectant is at least one member selected from the group consisting of sorbitol, glycerin and propylene glycol;

said desensitizing agent is at least one member selected from the group consisting of strontium chloride, potassium nitrate and sodium citrate-citric acid; and said preservative is at least one member selected from the group consisting of benzoic acid, butylated hydroxyanisole, butylated hydroxytoluene, ascorbic acid, methyl paraben, propyl paraben and tocopherol.

13. The method of claim 12, wherein:

said flavoring agent is at least one member selected from the group consisting of mints, citrus flavors, artificial vanilla, cinnamon, fruit flavors and anethole;

said coloring agent is at least one member selected from the group consisting of natural food colors and dyes suitable for use in foods, drugs and cosmetics; and said opacifier is titanium dioxide.

14. The method of claim 12, wherein the acid and corresponding salt of said buffering system are members selected from the group consisting of citric acid-sodium citrate, phosphoric acid-sodium phosphate, sodium monobasic phosphate and sodium dibasic phosphate, acetic acid-sodium acetate, succinic acid-sodium succinate, aconitic acid-sodium aconitate and benzoic acid-sodium benzoate.

* * * * *